US010393430B2

(12) United States Patent
Tremblay et al.

(10) Patent No.: US 10,393,430 B2
(45) Date of Patent: Aug. 27, 2019

(54) METHOD AND SYSTEM TO CONTROL THE METHANE MASS FLOW RATE FOR THE PRODUCTION OF LIQUEFIED METHANE GAS (LMG)

(71) Applicant: RTJ TECHNOLOGIES INC., Montreal (CA)

(72) Inventors: Charles Tremblay, Montreal (CA); Alain Roy, Montreal (CA); Simon Jasmin, Montreal (CA)

(73) Assignee: RTJ TECHNOLOGIES INC., Montreal, Quebec (CA)

( * ) Notice: Subject to any disclaimer, the term of this patent is extended or adjusted under 35 U.S.C. 154(b) by 403 days.

(21) Appl. No.: 15/260,729

(22) Filed: Sep. 9, 2016

(65) Prior Publication Data
US 2017/0074583 A1 Mar. 16, 2017

(30) Foreign Application Priority Data

Sep. 11, 2015 (CA) ..................................... 2903679

(51) Int. Cl.
*B01F 5/00* (2006.01)
*F25J 1/00* (2006.01)
(Continued)

(52) U.S. Cl.
CPC ............ *F25J 1/0022* (2013.01); *B01D 53/02* (2013.01); *B01F 3/02* (2013.01); *B01F 15/0022* (2013.01);
(Continued)

(58) Field of Classification Search
CPC .. B01F 3/02; B01F 3/026; B01F 3/028; B01F 2005/0017; B01F 2005/0022;
(Continued)

(56) References Cited

U.S. PATENT DOCUMENTS 2,823,523 A 2/1958 Eakin et al.
3,081,818 A * 3/1963 Braconier ................. B01F 3/02
431/346

(Continued)

FOREIGN PATENT DOCUMENTS

CN 103353207 A 10/2013
WO 2015196295 A1 12/2015

OTHER PUBLICATIONS

Ruhemann M: "Cryogenic Techniques in Enhanced Recovery of Oil and Gas", Indian Journal of Cryogen, Indian Cryogenics Council, Calcutta, India, vol. 9, No. 4, Jan. 1, 1984, pp. 256-261, XP008007141, ISSN: 0379-0479.

(Continued)

*Primary Examiner* — Marc C Howell
(74) *Attorney, Agent, or Firm* — IPAXIO S.E.N.C.

(57) ABSTRACT

The system is provided for generating a mixed methane gas feed stream using at least one source of biogas and an alternate source of methane gas. The system includes a biogas subsystem, a control device for the methane gas from the at least one alternate source of methane gas, and a vertically-extending gas mixing vessel. A method of controlling a methane gas mass flow rate of a mixed methane gas feed stream is also disclosed. The proposed concept is particularly well adapted for situations where an uninterrupted and relatively constant input of methane gas is required to ensure an optimum operation of, for instance, a LMG production plant.

14 Claims, 7 Drawing Sheets

(51) Int. Cl.
| | | |
|---|---|---|
| *B01F 3/02* | (2006.01) | |
| *C10L 3/10* | (2006.01) | |
| *B01D 53/02* | (2006.01) | |
| *B01F 15/00* | (2006.01) | |
| *B01F 15/02* | (2006.01) | |
| *F25J 1/02* | (2006.01) | |
| *G01N 30/86* | (2006.01) | |
| *G01N 30/02* | (2006.01) | |

(52) U.S. Cl.
CPC .. *B01F 15/00142* (2013.01); *B01F 15/00162* (2013.01); *B01F 15/00259* (2013.01); *B01F 15/00331* (2013.01); *B01F 15/0261* (2013.01); *C10L 3/10* (2013.01); *F25J 1/0052* (2013.01); *F25J 1/0212* (2013.01); *F25J 1/0255* (2013.01); *F25J 1/0262* (2013.01); *G01N 30/8675* (2013.01); *B01F 2005/0014* (2013.01); *B01F 2005/0022* (2013.01); *F25J 2205/04* (2013.01); *F25J 2210/02* (2013.01); *F25J 2210/04* (2013.01); *F25J 2210/60* (2013.01); *F25J 2210/66* (2013.01); *F25J 2215/60* (2013.01); *F25J 2220/66* (2013.01); *F25J 2230/30* (2013.01); *F25J 2240/40* (2013.01); *F25J 2270/66* (2013.01); *G01N 2030/025* (2013.01)

(58) Field of Classification Search
CPC ...... B01F 2005/0045; B01F 2005/0048; B01F 2005/0014; B01F 5/0071; F25J 1/0255; F25J 2210/02; F25J 2210/04; F25J 2210/66; F25J 2210/60; B01D 53/00; F01N 3/206; F23G 7/065
USPC .............................. 366/173.1, 107
See application file for complete search history.

(56) References Cited

U.S. PATENT DOCUMENTS

| | | | |
|---|---|---|---|
| 3,098,704 A * | 7/1963 | Schoppe | ............... B01F 3/0092 422/624 |
| 3,596,472 A | 8/1971 | Streich | |
| 3,702,619 A * | 11/1972 | Son | ........................ B01F 5/0456 137/3 |
| 3,874,184 A | 4/1975 | Harper et al. | |
| 4,230,469 A | 10/1980 | Grimm et al. | |
| 4,238,211 A | 12/1980 | Stuart | |
| 4,411,677 A | 10/1983 | Pervier et al. | |
| 4,415,345 A | 11/1983 | Swallow | |
| 4,496,382 A | 1/1985 | Geist et al. | |
| 4,501,600 A | 2/1985 | Pahade | |
| 4,504,295 A | 3/1985 | Davis et al. | |
| 4,662,919 A | 5/1987 | Davis | |
| 4,681,612 A | 7/1987 | O'Brien et al. | |
| 4,987,744 A | 1/1991 | Handley et al. | |
| 5,535,594 A | 7/1996 | Grenier | |
| 5,642,630 A | 7/1997 | Abdelmalek et al. | |
| 6,199,403 B1 | 3/2001 | Cole et al. | |
| 6,223,557 B1 | 5/2001 | Cole | |
| 6,631,626 B1 | 10/2003 | Hahn | |
| 6,751,984 B2 | 6/2004 | Neeraas et al. | |
| 6,978,638 B2 | 12/2005 | Brostow et al. | |
| 7,520,143 B2 | 4/2009 | Spilsbury | |
| 8,381,544 B2 | 2/2013 | Coyle | |
| 9,023,131 B2 | 5/2015 | Tremblay et al. | |
| 10,214,702 B2 * | 2/2019 | Gerhold | .................... C10L 3/08 |
| 2006/0248921 A1 | 11/2006 | Hosford et al. | |
| 2007/0095099 A1 | 5/2007 | Paradowski | |
| 2010/0000234 A1 | 1/2010 | Bras et al. | |
| 2010/0058802 A1 | 3/2010 | Brendeng et al. | |
| 2012/0060554 A1 | 3/2012 | Schmidt | |
| 2012/0067079 A1 | 3/2012 | Sethna et al. | |
| 2014/0043932 A1 * | 2/2014 | Russell | .................. F23K 5/002 366/160.1 |
| 2015/0285553 A1 | 10/2015 | Oelfke et al. | |
| 2017/0102182 A1 | 4/2017 | Tremblay et al. | |

OTHER PUBLICATIONS

Extended European Search Report in EP15812354.7 (EP3161113) dated Jun. 16, 2017.
Machine translation in English of CN103353207A.

* cited by examiner

METHOD AND SYSTEM TO CONTROL THE METHANE MASS FLOW RATE FOR THE PRODUCTION OF LIQUEFIED METHANE GAS (LMG)

CROSS-REFERENCE TO PRIOR APPLICATION

The present case claims the benefit of Canadian patent application No. 2,903,679 filed on 11 Sep. 2015, which is hereby incorporated by reference in its entirety.

TECHNICAL FIELD

The technical field relates generally to methods and systems to control a methane gas feed stream for the production of Liquefied Methane Gas (LMG) where there is more than one possible methane gas source.

BACKGROUND

Natural gas is a hydrocarbon gas mixture that is generally used as a source of energy. Natural gas includes mostly methane ($CH_4$) in high concentrations, such as about 85% vol. for instance, with the balance of the gas stream including gases such as ethane, propane, higher hydrocarbon components, a small proportion of water vapor, nitrogen and/or carbon dioxide. Other components such as mercury, hydrogen sulfide and mercaptan can also be present in lower concentrations. Variants are possible.

Natural gas can be compressed and transported in gas pipelines but it can also be converted from its primary gas form to a liquid form at cryogenic temperatures for ease of storage and transportation. Liquefied natural gas (LNG) takes considerably less volume than natural gas in a gaseous state. This makes LNG more cost efficient to transport over long distances where natural gas pipelines do not exist.

LNG is increasingly used as an alternative fuel for transportation since it offers many advantages over other available kinds of fuel. For instance, it is an alternative fuel cleaner than other fossil fuels, with lower emissions of carbon and lower particulate emissions per equivalent distance traveled. LNG is also generally more energy efficient and provides a significant increase in the useful life of the engines. However, despite all its advantages, the widespread use of LNG in transportation faces several limitations due in most part to a lack of availability. There are a limited number of LNG production plants and a corresponding limited number of distribution points, i.e. fueling stations, particularly outside densely populated areas. Still, transporting LNG over long distances in relatively small quantities to supply remote fueling stations lowers environmental and economic benefits of LNG.

Natural gas is only one among a number of different possible sources of methane gas required for the production of LNG. For instance, landfill sites and anaerobic digesters can each generate significant amounts of biogas which contains methane gas, generally in concentration ranging from about 40 to 65% vol. under favorable operating conditions. Other gases that are mainly present in biogas include carbon dioxide, generally in concentration up to about 50% vol. of the gas stream, and nitrogen in concentration generally varying from a few percent to about 30% vol. of the gas stream. Other gases possibly present in smaller concentrations include oxygen, generally in concentration up to about 3% vol. of the gas stream, and hydrogen sulfide in concentration that are generally up to about 0.5% vol. of the gas stream. Other components can be present in even smaller concentrations, such as siloxanes, mercury, volatile organic carbons (VOC) and mercaptan. These compositions and concentrations are only examples. Variants are possible. Biogas originating from a landfill site or an anaerobic digester is generally saturated in water at the pressure and temperature conditions occurring at the capture points.

The methane gas fraction contained in biogas can be transformed into Liquefied Methane Gas (LMG). LMG can provide an equivalent to LNG in terms of quality and energy content. Thus, one could use LMG instead of LNG at fueling stations. This is particularly useful since biogas can be obtained locally almost anywhere, particularly from municipal landfill sites. Transforming biogas into LMG using small distributed production plants would then be highly desirable since this will promote an increase in the total number of fueling stations and solve supply issues in remote areas. It can also offer significant environmental and economic benefits over burning biogas in gas flares or releasing unburned biogas directly into the atmosphere.

Despite the fact that biogas is available almost everywhere and can be a very suitable low-cost alternative to natural gas as a source of methane gas, biogas is still rarely used for the production of LMG. This is due in most part to numerous challenges associated with the transformation of the methane gas fraction contained in biogas into LMG and that are unique to biogas. One of these challenges is the unpredictability of the biogas in terms of its total mass flow rate and the proportion of the methane gas fraction therein, particularly when biogas is captured in a landfill site. The concentration of the methane gas in the biogas collected from a landfill site may sometimes be insufficient to transform it into LMG. Air infiltrations can also lower the concentration and make the methane gas feed stream difficult to treat before entering a LMG production plant. Both situations may even occur simultaneously.

In landfill sites, the biogas composition and the methane gas concentration constantly fluctuate over time due to environmental factors, such as atmospheric pressure and temperature to name just a few. Cold weather conditions can also cause some collector pipes to freeze, thereby limiting biogas capture rate. Fluctuations also occur throughout the years since the decay of the organic matter within the landfill site will naturally diminish if no new waste materials is added. The water content within the organic matter may also diminish over time and cause the methane gas yield to drop.

In anaerobic digesters, the biogas composition and the methane gas concentration will often depend on the quality of the waste material supplied therein and their temperature. For instance, the methane gas concentration in the biogas tend to be lower under cold weather conditions. Other factors may exist. Hence, the biogas coming out of anaerobic digesters can fluctuate as well.

Existing LMG production plants are almost always custom designed and they rely on a methane gas source that is substantially stable. They are typically designed to provide a constant output capacity or to provide a capacity within a restricted range so that even a small LMG production plant requires a minimum mass flow rate of methane gas at any given time to be economically feasible and this can often be difficult to obtain. LMG production plants also often require many hours to restart after an interruption in order to reach their optimum production conditions. Thus, having an uninterrupted operation is thus highly desirable.

Notwithstanding the environmental factors, a LMG production plant can experience a methane gas shortage if they share the methane gas yield from a same biogas-generating site with another existing waste-to-energy project. For instance, if a greenhouse uses biogas for heating, the quantity of remaining methane gas available for the LMG production plant can be insufficient during certain parts of the year, given the fact that the heating requirements are the highest during cold weather conditions and this often coincides with a decrease in the methane gas yield. This problem may prevent the installation of the LMG production plant and the surpluses of methane gas coming out of the biogas-generating site will not become useful energy. Waste-to-energy facilities are generally not scalable and even an increase in the methane gas yield may not justify using the surplus in a LMG production plant. Significant increases in the methane gas yield can take years to happen. The same situation can happen when a new landfill site is opened. The biogas generation may take years to reach a certain level and the methane gas yield is not proven in advance.

Since the volume of biogas and the mass flow rate of its methane gas fraction continuously fluctuate, it can be desirable to rely on an alternative source of methane gas to compensate for the shortages. The methane gas yield can even stop without warning and it may be necessary to rely solely on the alternative source of methane gas for a given time. Hence, the biogas stream can represent between 0 and 100% of the total methane gas stream sent to be LMG production plant and the proportion of the alternative source of methane gas consequently varies between 0 and 100% as well. The gas supply must accept all possible scenarios and must also mix gases from two or more sources to create the required mixed methane gas feed stream.

Mixing together two or more different streams of gas is not always a simple task and a designer can be faced with many challenges, especially when the proportion of each gas stream can vary greatly. Existing gas mixers normally mix a percentage of a secondary gas into a predominant primary gas.

One more challenge is the mixing two sources of methane gas that are under different conditions. For instance, the various gas streams may have different temperatures prior to their mixing. Mixing natural gas and biogas will generally occur at a lower pressure compared to the supply pressure of the natural gas. The pressure drop resulting from the gas expansion will cause the temperature of the natural gas to decrease significantly. However, since biogas is normally saturated with water vapor, mixing the cold natural gas stream with a biogas stream can cause condensation of water vapor present in the biogas stream. The condensate will need to be separated from the mixed methane gas feed gas stream. Still, snow or even ice may form under certain conditions, such as when the pressure drop of the natural gas is relatively important and when the mass flow rate of the biogas is not sufficient to keep the temperature of the mixed methane gas feed stream above the freezing point. Such situation can result in a blockage and even interrupt the methane gas stream to the LMG production plant. It is thus desirable to prevent such situation from happening.

Another desirable feature would be to have a gas supply that is generic enough to operate under a wide range of different conditions without the need of extensive modifications.

Accordingly, there is still room for many improvements in this area of technology.

SUMMARY

The proposed concept can simultaneously address at least many of the challenges and limitations of existing approaches. It provides a way of controlling the numerous sources of methane feed gas to be supplied to a LMG production plant under an extremely wide range of possible concentrations between biogas coming from a biogas source and an alternative methane gas source. The alternative methane gas source, for instance natural gas, can compensate fluctuations in the methane gas yield and even be used as the sole source of methane gas in certain conditions. The proposed concept further involves using a gas mixing vessel, even when only one methane gas source is used. When mixing biogas with the methane gas stream coming from an alternative methane gas source, the gas mixing vessel provides an intimate mixing of the gases and separates the condensate from the mixed methane gas feed stream before it exists.

In accordance with one aspect, there is provided a gas supply system for generating a mixed methane gas feed stream using at least one source of biogas and at least one alternate source of methane gas, the gas supply system including: a biogas subsystem; a control device for the methane gas coming from the at least one alternate source of methane gas; and a vertically-extending gas mixing vessel having an upper biogas inlet that is selectively in fluid communication with an outlet of the biogas subsystem, at least two vertically spaced-apart mid-level gas inlets that are each selectively in fluid communication with the control device for the methane gas coming from the at least one alternate source of methane gas, a bottom condensate outlet, and a mixed methane gas feed stream outlet that is located vertically above the mid-level gas inlets.

In accordance with another aspect, there is provided a method of controlling a mixed methane gas feed stream, coming from at least one source of biogas and an alternate source of methane gas, to supply a Liquefied Methane Gas (LMG) production plant, the method including: receiving biogas from the at least one source of biogas as a primary source of methane gas; measuring biogas pressure and a methane gas concentration in the biogas received from the at least one source of biogas; supplying the biogas in a gas mixing vessel; measuring the pressure immediately at an outlet of the gas mixing vessel; and supplying methane gas from at least one alternate source of methane gas inside the gas mixing vessel so as to counterbalance a missing methane gas fraction in the biogas and in response at least in part of at least one among the measured biogas pressure and the methane gas concentration in the biogas received from the at least one source of biogas, wherein the methane gas content in the mixed methane gas feed stream coming from the at least one source of biogas and the methane gas content in the mixed methane gas feed stream coming from the at least one alternate source of methane gas can each vary in a proportion between 0 and 100% vol. of the mixed methane gas feed stream.

Further details on these aspects as well as other aspects of the proposed concept will be apparent from the following detailed description and the appended figures.

DETAILED DESCRIPTION

Figure 1:
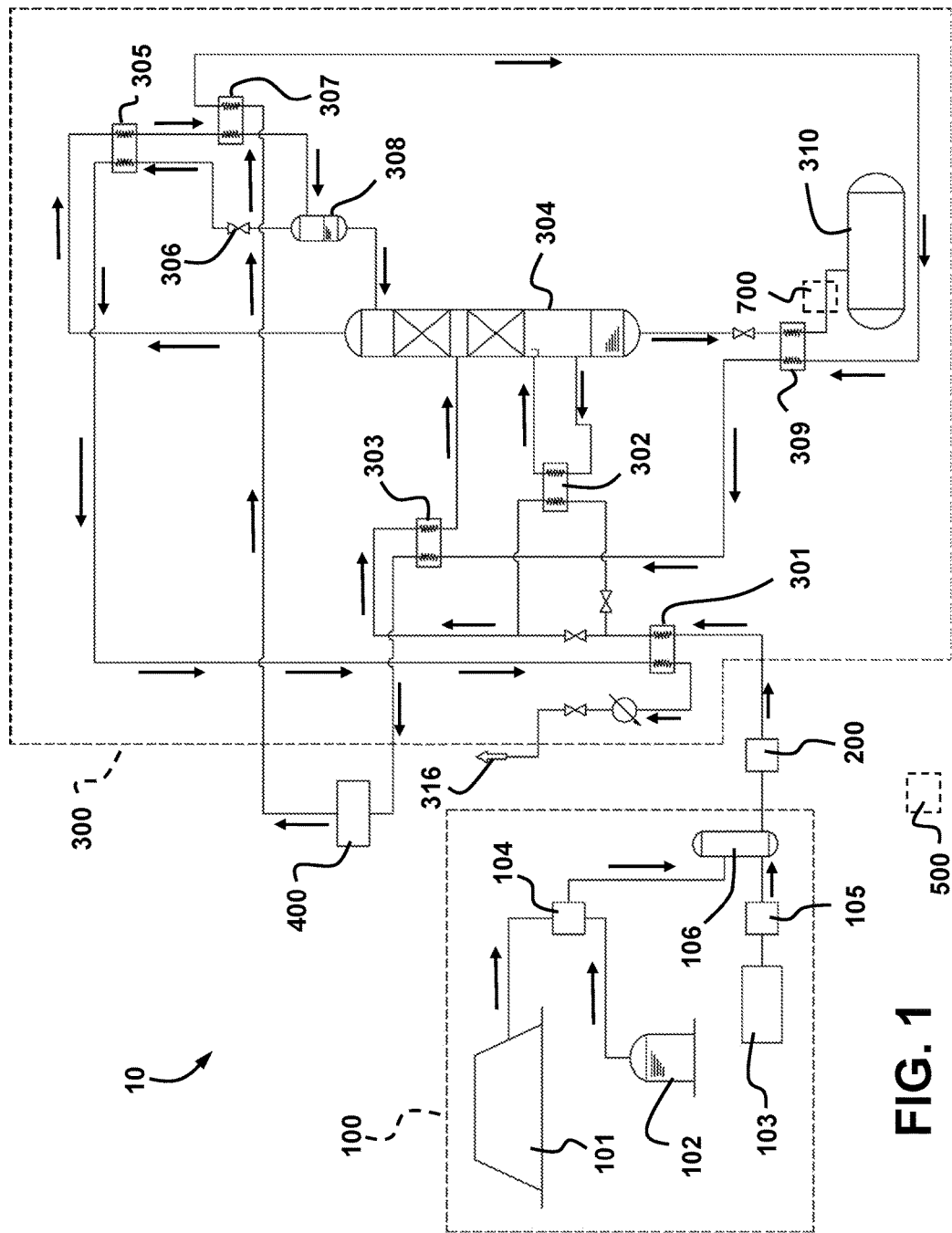
FIG. 1 is a semi-schematic view of an example of Liquefied Methane Gas (LMG) production plant.

FIG. 1 is a semi-schematic view of an example of Liquefied Methane Gas (LMG) production plant 10. For the sake of simplicity, it is illustrated as a simplified flow diagram. This LMG production plant 10 can be, for instance, like the one shown and described in Canadian Pat. No. 2,855,383 issued 23 Jun. 2015 to the same Applicant, or variants thereof. Canadian Pat. No. 2,855,383 is hereby incorporated by reference in its entirety.

Those skilled in the art will recognize that the appended figures only show some of the components that would be found in an actual commercial plant. Other components have been omitted for the sake of clarity. They may include, for example, valves, sensors and/or actuator motors, to name just a few. These other components will generally be included in actual implementations in accordance with standard engineering practice. They need not be described herein to gain and appreciate a full understanding of the proposed concept by those skilled in the art.

The LMG production plant 10 of FIG. 1 includes different integrated systems that are interconnected through a plurality of lines or pipes. It is designed to produce LMG using methane gas contained in a methane gas feed stream. This methane gas feed stream can be a mixture of gases from different gas sources and will now be referred to hereafter as the "mixed methane gas feed stream".

The arrangement illustrated in FIG. 1 is particularly well adapted for relatively small distributed LMG production plants, for instance those having a capacity ranging from about 400 to 15,000 MT per year, and/or when the mixed methane gas feed stream has a wide range of possible nitrogen-content proportions, including one where nitrogen is substantially absent. The proposed concept can also be very useful in the design of medium-scale and/or large-size plants, including ones where the nitrogen content always remains above a certain threshold. The methods and arrangements proposed herein can mitigate losses of methane gas when venting nitrogen, for instance in the atmosphere.

As can be appreciated, the proposed concept provides a gas supply system and a gas supply method that are sufficiently versatile for use under a very wide range of operating conditions, regardless of the source of methane-containing gas and of the rate of the variations. The mixed methane gas feed stream can be used for producing LMG. It is particularly well adapted for situations where an uninterrupted and relatively constant input of methane gas is required to ensure an optimum operation and where such optimum operation can take a time to obtain after an interruption. An infrastructure for producing LMG, such as the LMG production plant 10 of FIG. 1, is one example of such situation. Others are possible as well.

It should be noted that as used herein, the term "biogas" generally refers to a gas generated by the biodegradation of organic matter, for instance gas coming from a landfill site, from an anaerobic digester, and/or from any other similar suitable source or sources of methane gas other than a source of natural gas. In the illustrated examples, two biogas sources are used in parallel, one being a landfill site 101 and another being an anaerobic digester 102. Both include capture points. If desired, some implementations can be designed for use with only one possible source of biogas instead of two, as shown. Additional sources of biogas can be provided as well.

As used herein, the expression "alternate source of methane gas" generally refers to any suitable source of gas comprising mostly methane, for instance one having a methane gas concentration of 85% vol. Variants are also possible. In the illustrated examples, the alternate source of methane gas is a natural gas pipeline 103 from which a highly pressurized natural gas can be obtained. The natural gas pipeline can also be replaced and/or used in combination with a storage tank or the like. For instance, the storage tank can include a LMG storage tank at the end of the LMG production plant 10. The methane gas from the alternate source of methane gas is thus not necessarily always natural gas, such as natural gas coming from a natural gas pipeline. The expression "natural gas" is mainly used in the present detailed description only because the illustrated examples are showing implementations where the alternate source of methane gas is the natural gas pipeline 103.

As used herein, the expression "mixed methane gas feed stream" as well as other related words and expressions generally refer to a methane gas feed stream at the inlet of the LMG production plant whose content originates from a variety of possible sources. However, this does not imply that the methane gas content must be a mixture of gases from two or more different sources at any given moment. It is still possible to have the methane gas content coming from only one of the sources during a certain time period and this gas stream will nevertheless be referred to as the "mixed methane gas feed stream" in the context.

The illustrated LMG production plant 10 of FIG. 1 includes a gas supply system 100. The gas supply system 100 outputs the mixed methane gas feed stream from which LMG will be produced. The gases in the gas supply system 100 flow through a network of lines and pipes providing a fluid communication between the various components. Gases entering the gas supply system 100 are thus biogas and/or natural gas, each in a proportion between 0 and 100% vol.

When needed, such as when biogas cannot supply enough methane gas, an alternate source of methane gas can used to supply the missing methane gas fraction or even to supply all the methane gas. The methane gas fraction in the biogas coming from landfill sites often continuously fluctuates and it may even fall too low for the amount of LMG to be produced. The missing methane gas fraction can then be obtained from the alternate source of methane gas until it is no longer needed. Other possible situations include a sudden rise in the demand in LMG. The biogas and/or the natural gas, depending on the source or sources being used, are mixed into a vertically-extending gas mixing vessel 106.

In the landfill site 101, a mixture of raw biogas and leachate generally enters the capture points and this mixture is collected using a network of conduits provided across the landfill site 101. Once captured, biogas is sent to a biogas compression, control and primary treatment subsystem 104. This biogas subsystem 104 can include, for instance, one or more hydrostatic multi-phase separators 202, such as those shown and described in the U.S. Pat. No. 9,023,131 issued on 5 May 2015, in which the leachate fraction of the mixture is separated from the gas fraction. U.S. Pat. No. 9,023,131 is hereby incorporated by reference in its entirety. Variants are possible as well.

The biogas coming from the anaerobic digester 102 is continuously generated and accumulates at the top where it is collected.

The biogas subsystem 104 may include various components such as a low pressure compressor and a corresponding gas cooling unit. The low pressure compressor increases the pressure of the biogas, for instance to about 100 kPag. Other pressure values are possible as well. In the illustrated examples, the biogas coming from the landfill site 101 and the biogas coming from the anaerobic digester 102 are both compressed and cooled by the same equipment. Variants are possible as well.

In the illustrated examples, an outlet of the natural gas pipeline 103 is connected to a control device 105. This device 105 controls the supply and flow rate of the natural gas coming from the natural gas pipeline 103. In other implementations, the control device 105 can be used to control the methane gas coming from at least one other alternate source of methane gas that is not a natural gas pipeline. The schematic boxes 103 in the figures can also represent such other alternate source of methane gas.

The output of the gas supply system 100 corresponds to the output of the gas mixing vessel 106. As shown in FIG. 1, the mixed methane gas feed stream can be supplied to a gas treatment system 200. The gas treatment system 200 is provided, among other things, to increase pressure and to remove some undesirable components from the mixed methane gas feed stream. Undesirable components can include, for instance, carbon dioxide, hydrogen sulfide (often called acid gases), siloxanes, VOC and mercury. Variants are possible as well. It is generally desirable that the absorption acid gas removal subsystem brings the carbon dioxide concentration under about 50 ppmv and the hydrogen sulfide ($H_2S$) concentration under about 2 ppmv before the mixed methane gas feed stream enters the LMG production and nitrogen rejection system 300. Variants are possible as well.

The gas treatment system 200 can include, for instance, an absorption acid gas removal subsystem operating at a relatively low pressure, such as a pressure of less than about 100 kPag (14.5 psig). Other values are possible. The absorption acid gas removal subsystem can use an aqueous amine solvent to remove carbon dioxide and hydrogen sulfide as a result of a chemical reaction process. Biogas can also be subjected to a pretreatment within the biogas subsystem 104, for instance, to remove at least some of the $CO_2$ and the $H_2S$ present in the biogas stream. Variants are possible as well.

The gas treatment system 200 generally includes a high pressure compressor. The expression "high pressure", as used in the context of this compressor, generally refers to the highest pressure in the LMG production plant 10. The pressure range will generally be from about 1,380 kPag to 2,070 kPag. Other values are possible. However, the magnitude of these pressures is significantly lower than the magnitude of the pressures involved in many existing arrangements. Using pressures within these lower pressure ranges will considerably decrease the costs of the compressor and its energy consumption. It should be noted that depending on the implementation, the compressor can either be a single compressor or a unit integrating two or more compressors. Both situations are covered within the meaning of the word "compressor", even if used in a singular form.

The mixed methane gas feed stream coming out of the system 200 enters the LMG production and nitrogen rejection system 300. At this point, the pressurized mixed methane gas feed stream contains mostly methane and possibly nitrogen. Nitrogen will generally have a possible concentration between one where nitrogen is totally or almost totally absent and about 50% vol. The very low nitrogen concentrations would occur, for instance, when the mixed methane gas feed stream comes only from the alternative source of methane gas, such as the natural gas pipeline 103.

The system 300 includes various components to condense the methane gas, separate the nitrogen (if any) from the condensed methane gas, and cool the condensed purified methane gas product, constituting at that point the LMG, down to a storage temperature. The system 300 is well integrated with the other systems in the LMG production plant 10 in order to improve the efficiency of the whole process.

The mixed methane gas feed stream is carried in the system 300 through a network of lines and pipes of a mixed methane gas feed stream circuit. The mixed methane gas feed stream then passes, in succession, at least through a first heat exchanger 301 and a second heat exchanger 303. The second heat exchanger 303 is located downstream the first heat exchanger 301. The circuit goes from the outlet of the second heat exchanger 303 to a mid-level inlet of a fractional distillation column 304.

Before entering the fractional distillation column 304, the mixed methane gas feed stream is cooled down to a cryogenic temperature. The cryogenic temperature will condense the methane gas in the second heat exchanger 303, for example to about −120 to −140° C., typically about −130° C. Most of the nitrogen, if any is present in the mixed methane gas feed stream, will still be in a gaseous form at the outlet of the second heat exchange 303 before its introduction in the mid-level inlet of the fractional distillation column 304. Therefore, the fractional distillation column 304 makes a separation of the two fractions, one being a methane-rich liquid fraction and the other being a nitrogen-rich gas fraction. The methane-rich liquid fraction will accumulate at the bottom of the fractional distillation column 304 and can be withdrawn through a bottom outlet of the fractional distillation column 304. This methane-rich liquid fraction constitutes the LMG. With the system 300, the LMG output can always be substantially exempt of nitrogen, for example with a maximum concentration in the order of about 1 to 3% vol.

The system 300 also includes a LMG circuit having a number of lines or pipes to convey the LMG. From the bottom outlet of the fractional distillation column 304, the LMG circuit passes through a third heat exchanger 309 that is provided to further cool the LMG to its final conditions, for example to a temperature of about −160° C. In the illustrated examples, the LMG circuit ends at a storage tank 310 in which it can stored and eventually be pumped to a potential user of the LMG. Variants are possible as well.

The system 300 further includes a nitrogen-rich gas fraction circuit having a number of lines or pipes to convey a nitrogen-rich gas fraction captured at a top outlet of the fractional distillation column 304. From this top outlet, the circuit passes through, in succession, a fourth heat exchanger 305 and a fifth heat exchanger 307. It ends at a mid-level inlet of a nitrogen phase separator vessel 308. This nitrogen phase separator vessel 308 includes a bottom outlet and a top outlet. The bottom outlet is in fluid communication with and positioned vertically above an overhead inlet of the fractional distillation column 304. Variants are possible as well.

In use, at least a portion of the nitrogen-rich gas fraction coming out of the top outlet of the fractional distillation column 304 undergoes a phase change to a liquid phase inside the fifth heat exchanger 307. A portion of the nitrogen-rich gas fraction can also undergo a phase change to a liquid phase inside the fourth heat exchanger 305.

The various heat exchangers of the system 300 use two distinct refrigerant circuits. An indirect heat exchange is carried out in each of these heat exchangers since no mixing of the fluids occur therein. The first refrigerant circuit of the LMG production plant 10 is an opened-loop refrigerant circuit for a first cryogenic refrigerant. Nitrogen coming out of the top outlet of the nitrogen phase separator vessel 308 constitutes this first cryogenic refrigerant. The first cryogenic refrigerant only passes once through the first refrigerant circuit. It passes, in succession, through an expansion valve 306, the fourth heat exchanger 305 and the first heat exchanger 301. It ultimately goes out of the first refrigerant circuit through a venting outlet 316.

In the illustrated examples, the venting outlet 316 vents the nitrogen directly into the atmosphere but it will be almost exempt from methane gas, for example less than about 1% vol. The goal is to bring the methane gas concentration as low as possible, preferably below about 2% vol. and even more preferably below about 1% vol. in the venting outlet 316. This will mitigate the loss of methane gas and therefore maximize the amount of LMG being produced.

As can be seen, the expansion valve 306 is in direct fluid communication with the top outlet of the nitrogen phase separator vessel 308. The expansion valve 306 can be for instance a Joule-Thomson control valve into which the pressure is greatly reduced between the inlet and the outlet of the expansion valve 306. The outlet pressure can be, for example, between about 70 to 170 kPag, generally from about 100 kPag, before being fed into the cold side of the fourth heat exchanger 305.

The second refrigerant circuit is a closed-loop circuit provided for a second cryogenic refrigerant. This second refrigerant circuit is separated from the first refrigerant circuit. The second refrigerant circuit is in fluid communication with an inlet and an outlet of an independent cryogenic refrigeration system 400. The second cryogenic refrigerant at its coldest temperature is first supplied through the inlet of the fifth heat exchanger 307. The second cryogenic refrigerant exits the fifth heat exchanger 307 and is supplied to the cold side of the third heat exchanger 309. The second cryogenic refrigerant exits the third heat exchanger 309 and is supplied to the cold side of the second heat exchanger 303. The second cryogenic refrigerant exits the second heat exchanger 303 to be returned to the inlet of the independent cryogenic refrigeration system 400.

The independent cryogenic refrigeration system 400 can be a multicomponent refrigerant cooled by a conventional two-flow plate heat exchangers and using a conventional oil lubricated compressor, for instance as disclosed in U.S. Pat. No. 6,751,984 (Neeraas et al.) of 2004, which is hereby incorporated by reference in its entirety. Other systems or kinds of systems can be used as well.

The illustrated system 300 further includes a sixth heat exchanger 302 and a reboiler circuit that is in fluid communication with the interior of the fractional distillation column 304. The reboiler circuit passes through the sixth heat exchanger 302 in which the reboiler circuit is in indirect heat exchange relationship with at least a portion of the mixed methane gas feed stream coming from a by-pass circuit. The by-pass circuit has an inlet and an outlet that are both provided, on the mixed methane gas feed stream circuit, downstream of the first heat exchanger 301 and upstream of the second heat exchanger 303. The reboiler circuit has an inlet that is vertically above the outlet in the fractional distillation column 304. In use, a portion of the mixed methane gas feed stream can be circulated from inside the fractional distillation column 304 through the reboiler circuit. The flow of main gas stream supplied to the sixth heat exchanger 302 is controlled by two flow control valves, a LMG reboiler control valve and a LMG bypass control valve. Variants are possible as well.

While the methane rich liquid flows by gravity through the internal packing of the fractional distillation column 304, upward methane gas will separate nitrogen gas from the methane-rich liquid fraction going down the fractional distillation column 304. Residual methane gas present into the nitrogen-rich gas fraction rising into the fractional distillation column 304 is liquefied using the cold liquid reflux stream supplied at the top of the fractional distillation column 304 and coming from the nitrogen phase separator vessel 308. The reflux stream content includes liquid methane and liquid nitrogen.

Figure 2:
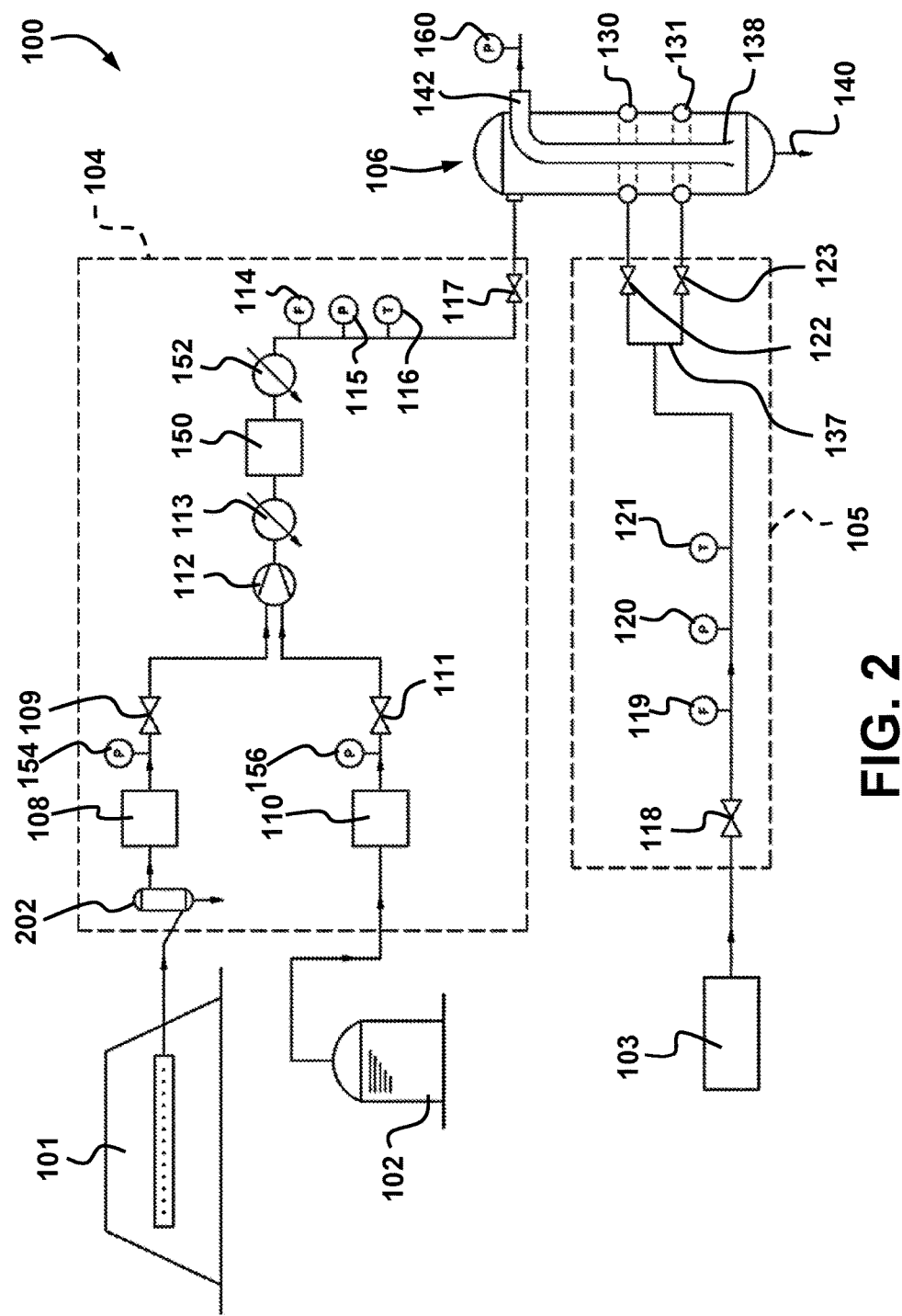
FIG. 2 is an enlarged semi-schematic view illustrating the details of an example of a gas supply system in accordance with the proposed concept.

FIG. 2 is an enlarged semi-schematic view illustrating the details of an example of a gas supply system 100 in accordance with the proposed concept. This example corresponds to what is shown more schematically in FIG. 1.

The gas supply system 100 of FIG. 2 includes gas composition analyzers 108, 110 to measure the methane gas content and also possibly the oxygen content in the biogas coming from the landfill site 101 and the anaerobic digester 102, respectively. The gas composition analyzers 108, 110 can be, for instance, gas chromatographs. Other kinds of devices and/or technologies are possible as well.

The gas supply system 100 of FIG. 2 also includes gas quality control valves 109, 111 to control the methane gas content in the biogas coming from the landfill site 101 and from the anaerobic digester 102, respectively, as a function of the demand. It is desirable to control the methane feed gas so that its methane gas content and the biogas pressure be kept above a desired set point. These valves 109, 111 can also be used to limit the oxygen content in the biogas to a maximum value, for example 0.5% vol. Keeping the oxygen concentration relatively low is generally desirable to mitigate the amount of $O_2$ that can combine with amines and deteriorate the amine process performance.

In FIG. 2, a biogas low pressure compressor 112 is provided to increase the pressure of the biogas, for example, to 100 kPag. Other values are also possible. The gases from the two biogas sources 101, 102 are combined in the compressor 112. The resulting biogas stream is cooled in a biogas cooler 113 located immediately downstream of the compressor 112. Then, biogas stream undergoes a pretreatment in a pretreatment unit 150. This can include, for instance, removing a portion of the $CO_2$ and of the $H_2S$ under low pressure conditions. Variants are possible as well. The biogas stream is further cooled in an additional cooling unit 152.

In FIG. 2, pressure sensors 154, 156 are provided at the outlet of the landfill site 101 and the anaerobic digester 102, respectively. The pressure sensor 154 is located between the gas composition analyzer 108 and the valve 109, and the pressure sensor 156 is located between the gas composition analyzer 110 and the valve 111. Variants in the position of the pressure sensors 154, 156 are possible as well. However, it is desirable that the pressure sensors 154, 156 be located upstream of the biogas low pressure compressor 112 since they can used in the control of the gas supply system 100. For instance, they can detect if the pressure falls under a threshold value when the demand of biogas is higher than what is available. This may occur if the biogas low pressure compressor 112 draws too much biogas. In general, if the pressure at the inlet of the landfill site 101 is too low, the methane gas fraction will decrease since the proportion of the other gases that may be present in the biogas will tend to increase, for example as result of air leaks. The outlet of the anaerobic digester 102 should also be kept at a pressure that is above a threshold value. Keeping the gas pressure above threshold values at the outlet of each source of biogas is thus generally desirable.

Various physical parameters are measured in the biogas stream prior to entering into the gas mixing vessel 106. This includes, in the example shown in FIG. 2, measuring the flow rate using a gas flowmeter 114, measuring the pressure using a pressure sensor 115 and measuring the temperature using a gas temperature sensor 116. The mass flow rate of the methane gas fraction contained in the biogas stream can be calculated from this data. Variants are possible as well.

Still, in the example shown in FIG. 2, the natural gas control device 105 includes a natural gas pressure reducing valve 118 to initially reduce the natural gas supply pressure under a constant value. It also includes a pressure sensor 120 to measure the pressure of the natural gas. It can also include a gas flowmeter 119 to measure the flow rate of natural gas and a gas temperature sensor 121 to measure the temperature of the natural gas. The initial pressure reduction of the natural gas is necessary for controlling the natural gas temperature prior to its injection into the gas mixing vessel 106. The mass flow rate of the methane gas fraction contained in the natural gas stream can be calculated from this data. Variants are possible as well.

Since the biogas is, in general, the primary source of methane gas and that the biogas contains water vapor that can condense following a temperature reduction, the gas mixing vessel 106 is configured in such a way that the secondary gas is injected into the primary gas, the biogas.

The biogas stream enters the gas mixing vessel 106 at an upper end. The flow of the biogas stream is controlled by a flow control valve 117. Once inside the inner chamber of the gas mixing vessel 106, the biogas stream will follow a path that goes towards the bottom of the gas mixing vessel 106, where it will enter the bottom opened end of an internal central conduit 138.

The natural gas enters the gas mixing vessel 106 using at least two vertically spaced-apart natural gas injection stages located vertically below the biogas stream inlet in the inner chamber within the gas mixing vessel 106. Each stage covers a range of proportions of the methane gas fraction coming from the natural gas compared to the total methane gas fraction in the mixed methane gas feed stream. When this range of proportions is as wide as from 0 to 100% vol., using two or more stages is desirable. For instance, the first stage can cover the range of 0 up to 25% vol. and the second stage can cover from 25 to 100% vol. Other values are possible and they may also overlap. With multiple stages, only one can be used when only a relatively small amount of natural gas is injected into the biogas stream, and one or more additional stages are used to inject the natural gas at multiple locations when larger amounts are needed. Also, using multiple stages can improve control precision.

The two stages form mid-level natural gas inlets 130, 131 of the gas mixing vessel 106. In the example illustrated in FIG. 1, the first natural gas injection stage includes a first circular distribution pipe 130 and the second natural gas injection stage includes a second circular distribution pipe 131. These two pipes 130, 131 are integrated into the wall of the gas mixing vessel 106 and disposed in a generally horizontal manner. Variants are possible as well.

In FIG. 2, the flow of natural gas going through the first injection stage is controlled by a control valve 122 and the flow of natural gas going through the second injection stage is controlled by a control valve 123. They are both located downstream of a common header 137. The natural gas come out of the circular distribution pipes 130, 131 through a plurality of corresponding calibrated orifices located all around the periphery thereof, for instance in an axisymmetric manner. The orifices are located in the upper inner quadrant of the circular distribution pipes 130, 131 to promote intermixing of the natural gas with the biogas stream flowing downwards inside the gas mixing vessel 106. Vanes or other mixing-promoting features can also be provided inside the gas mixing vessel 106. Vanes can promote a swirling motion and turbulences. Variants are possible as well. Obtaining a good mixture of the gases is desirable since this will promote uniformity of the gas temperatures and avoid the formation of distinct gas layers within the mixed methane gas feed stream at the outlet of the gas supply system 100.

In use, when mixing the biogas stream with a natural gas stream, the water vapor present into the generally water-saturated biogas stream can often condense due to the cold temperature of the natural gas stream due to a pressure drop, for instance from the natural gas pipeline 103 to the lower pressure inside the gas mixing vessel 106. The biogas stream will be increasingly prone to condensation as the proportion of natural gas in the mixed methane gas feed stream increases. When condensation occurs, the swirling motion of the gases and/or the turbulent conditions inside the gas mixing vessel 106 will promote adherence of the condensate particles on the inner wall of the gas mixing vessel 106 and on the surface of the other components therein. The condensate will then drip towards the bottom due to gravity and the gas flow occurring inside the gas mixing vessel 106. The condensate will accumulate at the bottom of the gas mixing vessel 106 and can be removed using a condensate outlet 140 or the like.

The mixed methane gas feed stream exits the gas mixing vessel 106 through the outlet 142, from which it can be feed to the LMG treatment system 200 (FIG. 1) or to another location, as required.

Overall, supplying methane gas from the natural gas pipeline 103 inside the gas mixing vessel 106 allows to counterbalance a missing methane gas fraction in the biogas. This can be made in response at least in part of at least one among the measured biogas pressure (measured for instance by the pressure sensors 154, 156) and the methane gas concentration (measured for instance by composition analyzers 108, 110) in the biogas received from the biogas sources 101, 102. Still, the methane gas content in the mixed methane gas feed stream coming from the biogas sources 101, 102 and the methane gas content in the mixed methane gas feed stream coming from the natural gas pipeline 103 can each vary in a proportion between 0 and 100% vol. of the mixed methane gas feed stream.

Figure 3:
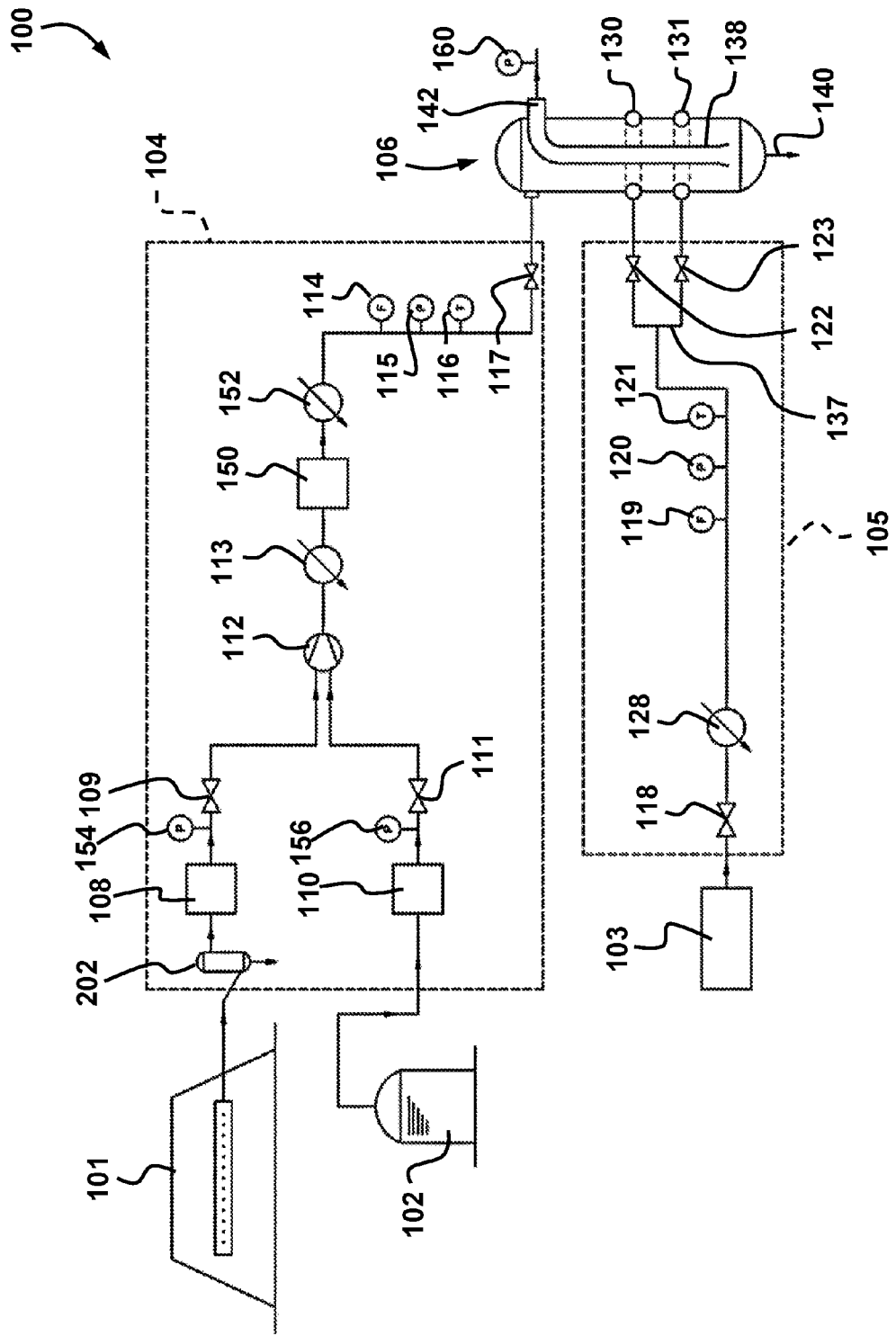
FIGS. 3 and 4 are views similar to FIG. 2 illustrating other examples of a gas supply system in accordance with the proposed concept.

FIG. 3 is an enlarged semi-schematic view illustrating the details of another example of the gas supply system 100 in accordance with the proposed concept. Some components of the gas supply system 100 illustrated in FIG. 3 are similar to corresponding components in the example illustrated in FIG. 2. However, in FIG. 3, the gas supply system 100 is designed for use with a natural gas source having a relatively high pressure before entering the gas supply system 100. The natural gas pressure is lowered down to a reduced pressure, for instance of 150 kPag, with a natural gas pressure reducing valve 118. A large pressure drop can cause a significant drop in the natural gas temperature. If such situation is encountered, the natural gas stream is then heated by a heating device 128 after expansion from the natural gas pressure reducing valve 118 and prior to entering the gas mixing vessel 106.

Figure 4:
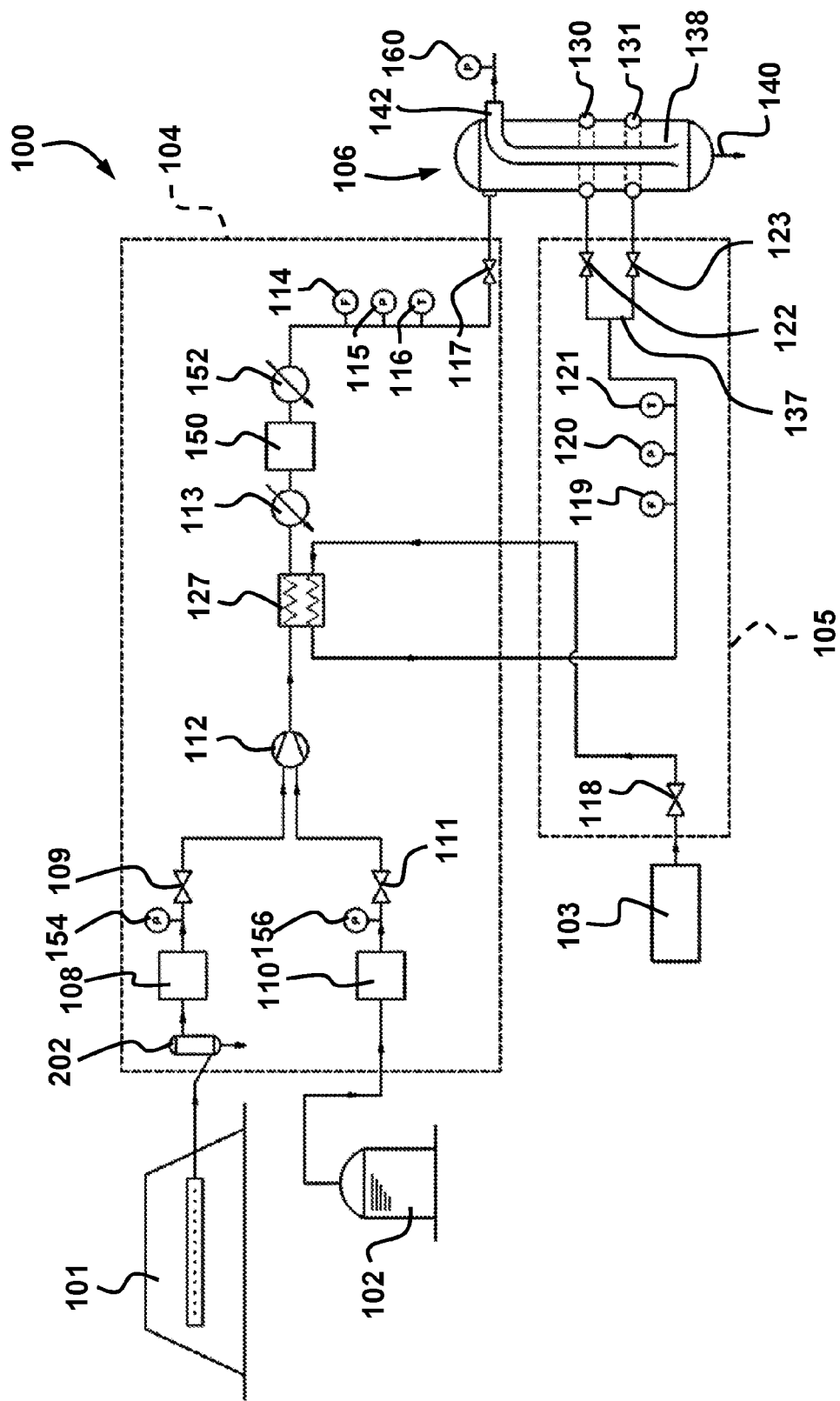

FIG. 4 is an enlarged semi-schematic view illustrating the details of another example of the gas supply system 100 in accordance with the proposed concept. Some components of the gas supply system 100 illustrated in FIG. 4 are similar to corresponding components in the example illustrated in FIG. 2. However, in FIG. 4, a heat exchanger 127 provides an indirect heat exchange relationship between the biogas stream and the natural gas stream. No mixing between the two gas streams occurs inside the heat exchanger 127 but the temperature difference will be reduced before entering the gas mixing vessel 106.

It should be noted that the concept is not limited to the examples shown in FIGS. 2 to 4. Other implementations are possible as well.

Figure 5:
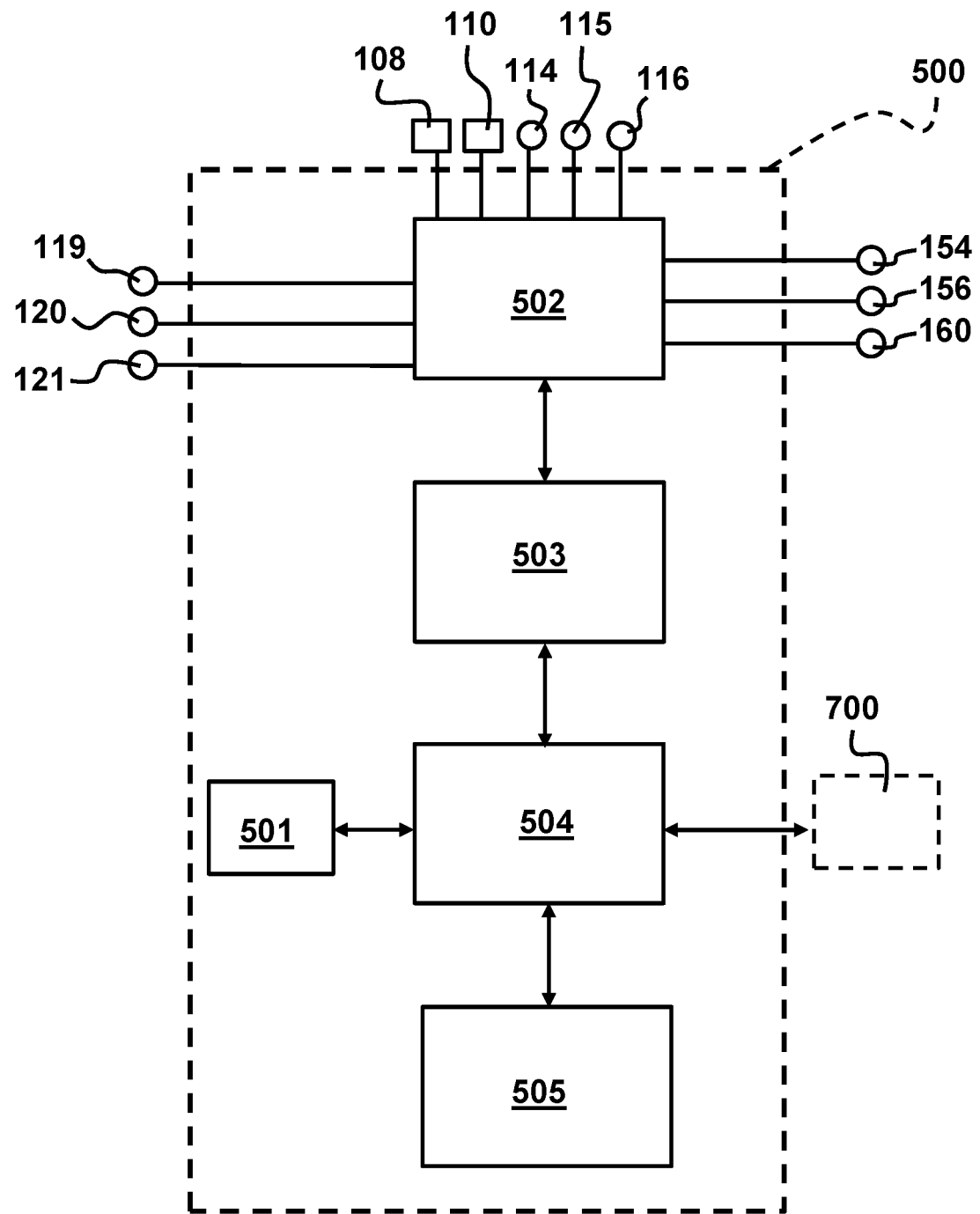
FIG. 5 is a simplified block diagram illustrating details of an example of a control system for the LMG production plant of FIG. 1.

FIG. 5 is a simplified block diagram illustrating details of an example of a control system 500 provided in the LMG production plant 10 of FIG. 1. Other kinds of configurations are possible as well. The illustrated control system 500 includes a LMG demand controller 501, a methane gas supply controller 502, a gas treatment system controller 503, a LMG production and nitrogen rejection system controller 504 and an independent cryogenic refrigeration system controller 505.

The methane gas supply controller 502 can actuate the mixed methane gas feed stream quality and quantity to satisfy the LMG demand controller 501. Signals can also be exchanged between the methane gas supply controller 502 and the other controllers 501, 503, 504, 505. The methane gas supply controller 502 can receive signals from different sensors and generate signals to various components, such as compressor motor, valves, etc. Variants are possible.

The gas treatment system controller 503 provides the gas treatment quality control to satisfy the LMG demand controller 501. The gas treatment system controller 503 can receive signals from various sensors and can send signals, for instance to the motor of a high pressure compressor in the gas treatment system 200 or others. Signals may also be exchanged between the gas treatment system controller 503 and the other controllers 501, 502, 504, 505. Variants are possible as well.

The LMG production and nitrogen rejection system controller 504 provides the LMG production and nitrogen rejection system control to satisfy the LMG demand controller 501. The LMG production and nitrogen rejection system controller 504 can receive signals from various sensors and can send signals, for instance to a LMG reboiler control valve, a LMG reboiler bypass control valve, the expansion valve 306 (FIG. 1), a LMG flow control valve, a nitrogen vent control valve and also to various other control commands. The sensors can be, for instance, sensors provided in a LMG mass flowrate measuring device 700 installed at the LMG outlet (FIG. 1). The device 700 can include a LMG composition analyzer, a LMG flowmeter, a LMG pressure sensor and a LMG temperature sensor. Signals are also be exchanged between the LMG production and nitrogen rejection system controller 504 and the other controllers 501, 502, 503, 505. Variants are possible as well.

The independent cryogenic refrigeration system controller 505 can provide the independent cryogenic refrigeration system 400 (FIG. 1) with some control to satisfy the LMG demand controller 501. The independent cryogenic refrigeration system controller 505 can receive signals from various sensors and others. Signals are also exchanged between the independent cryogenic refrigeration system controller 505 and the other controllers 501, 502, 503, 504. Variants are possible as well.

If desired, the five controllers 501, 502, 503, 504, 505 of the example can be programmed into one or more general purpose computers, dedicated printed circuit boards and/or other suitable devices otherwise configured to achieved the desired functions of receiving the data and sending command signal. Depending on the implementation, the five controllers 501, 502, 503, 504, 505 can be separate devices and/or can be integrated into one or more single device. Each controller 501, 502, 503, 504, 505 would then be, for instance, a portion of the software code loaded into the device. Each controller may include a control/display interface to access the control system 500.

The liquefaction demand controller 505 provides a process signal to control the opening of the biogas flow control valve 117 which can varies from 0 to 100% and the opening of the natural gas flow control valves 122, 123, 124 which can varies from 0 to 100%. Since the methane content of the biogas can varies constantly both in quantity and in concentration, the supply of natural gas can compensate the methane input to the liquefaction process on a continuous basis. The methane can be supplied 100% by a biogas source, 100% from the natural gas source or from any combination of a plurality of methane sources. With this system, it is possible to supply the liquefaction process with a constant methane mass flow rate. Biogas will generally be used in priority but if this is not sufficient, the natural gas source will compensate.

Figure 6:
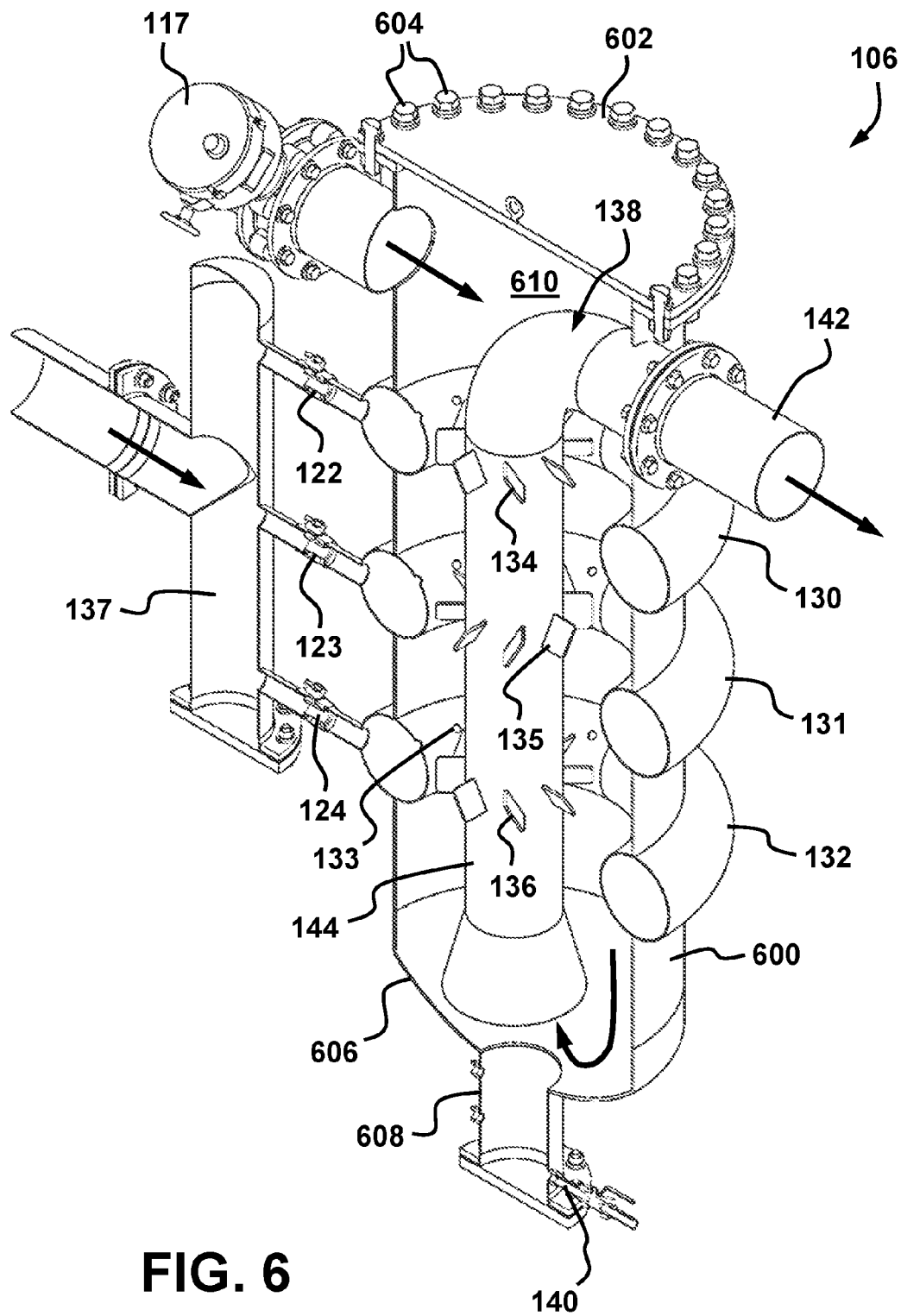
FIG. 6 is an isometric and partially cutaway view illustrating an example of a gas mixing vessel for use in a gas supply system in accordance with the proposed concept.
Figure 7:
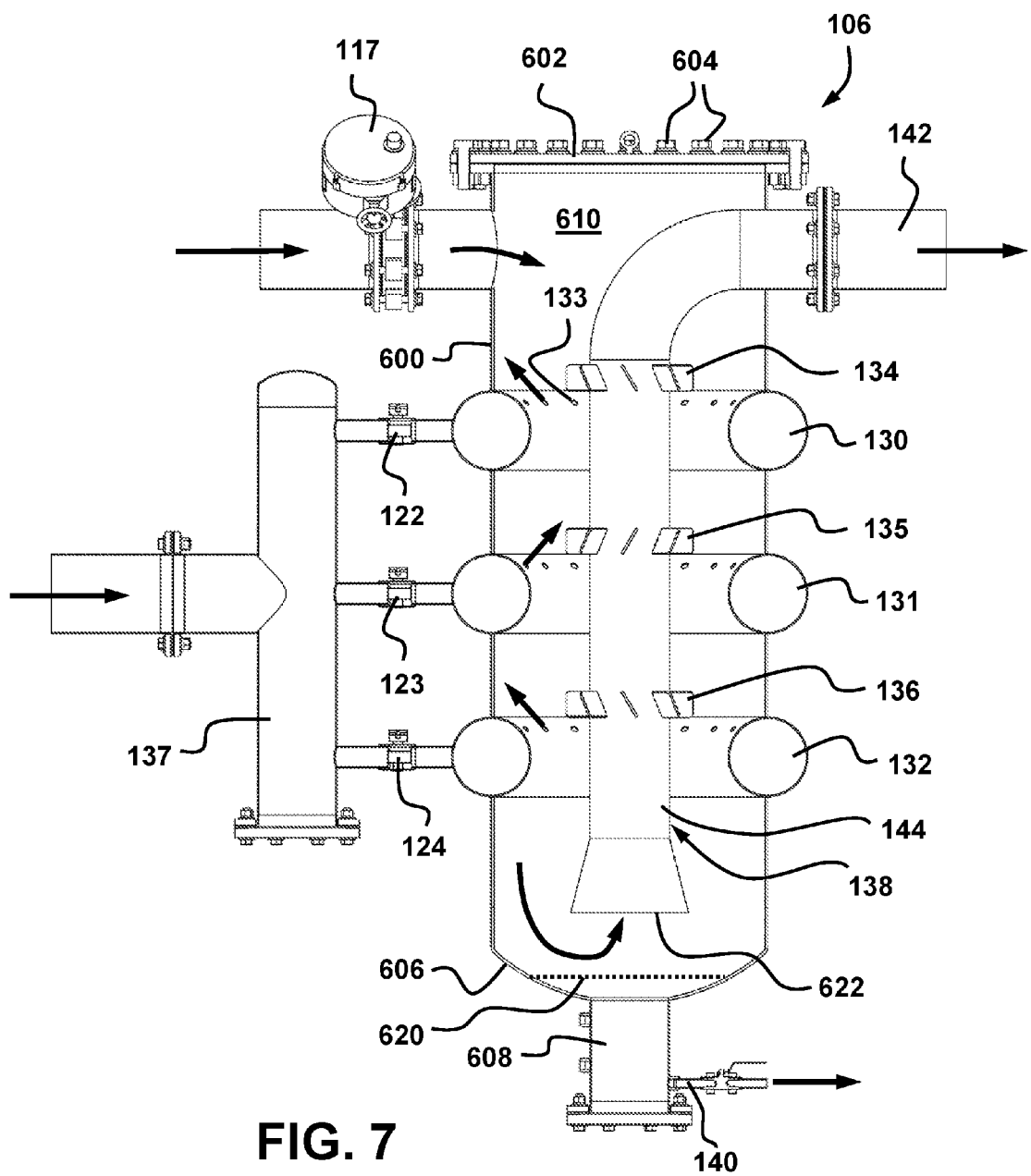
FIG. 7 is a side view of the gas mixing vessel of FIG. 6.

FIG. 6 is an isometric and partially cutaway view illustrating an example of a gas mixing vessel 106 for use in a gas supply system 100 in accordance with the proposed concept. FIG. 7 is a side view of the gas mixing vessel 106 of FIG. 6. Unlike the gas mixing vessel 106 schematically illustrated in FIGS. 2 to 4, the gas mixing vessel 106 in FIGS. 6 and 7 includes three vertically spaced-apart natural gas injection stages. The third natural gas injection stage includes a third circular distribution pipe 132. The flow of natural gas to the third circular distribution pipe 132 is controlled by a third control valve 124.

The calibrated orifices 133 are visible in FIGS. 6 and 7. These orifices 133 also create an expansion of the natural gas and promote turbulences, thereby improving the mixing within the gas mixing vessel 106.

FIGS. 6 and 7 further illustrate the vertically spaced-apart sets of axisymmetric vanes 134, 135, 136 that are rigidly attached directly around the main vertically-extending portion 144 of the internal central conduit 138. Variants are possible as well. The vanes 134, 135, 136 in this illustrated example have a same orientation within a same set but adjacent sets are oriented opposite to one another. The swirling motion of the second stage will thus be in a counter flow direction with reference to the other two stages in order to promote a more turbulent flow inside the gas mixing vessel 106 and increase the mixing occurring inside the gas mixing vessel 106.

FIGS. 6 and 7 also show that the illustrated gas mixing vessel 106 includes a cylindrical portion 600, an upper lid portion 602, attached onto the cylindrical portion 600 using a plurality of bolts 604, a funnel-shaped portion 606 welded or otherwise attached below the cylindrical portion 600, and a bottom end portion 608 welded or otherwise attached below the funnel-shaped portion. Variants are possible as well.

The various portions 600, 602, 606, 608 of the gas mixing vessel 106 form an inner chamber 610 in which the mixing occurs when biogas and natural gas are intermixed. If only one source of methane gas is used for a given period, the methane gas just passes through without any mixing occurring. However, the gas supply system 100 will be able to react very quickly as soon as the alternative methane gas source must be used. Always using the gas mixing vessel 106 in any situation also greatly simplifies the operations.

It should be noted that the gas mixing vessel 106 can be constructed differently for some implementations.

In use, the intimate mixing between the methane gas streams promotes the occurrence of uniform temperature. This way, if water or other fluids are likely to condensate, the condensation should occur inside the gas mixing vessel 106. The condensate can accumulate inside the bottom end portion 608 and the funnel-shaped portion 606. The condensate is retrieved through the condensate outlet 140. The condensate outlet 140 can include a conduit and a corresponding valve, as shown. Variants are also possible.

FIG. 7 schematically shows a condensate level 620. This level 620 is maintained below the bottom-opened inlet end 622 of the internal central conduit 138 so that the mixed methane gas stream can flow continuously out of the gas mixing vessel 106. This can be done using different devices, such as sensors, timers, etc. The bottom-opened inlet end 622 can be funnel-shaped, as shown, or be configured differently.

As can be appreciated, the gas mixing vessel 106 has no movable parts therein and is therefore not prone to failure.

If desired, some implementations can be designed for use with only one possible source of biogas instead of two, as shown. Additional sources of biogas and/or additional alternate sources of methane gas can be provided. If desired, the natural gas pipeline can also be replaced by a storage tank or the like.

EXAMPLES

The following are non-limiting examples, obtained from process simulations, to show the control of the mixed methane gas feed stream for the production of liquefied methane gas (LMG) using a plurality of methane gas sources. The examples are based on the implementation depicted in FIG. 2. The LMG production plant 10 is required to produce 10 tons per day of LMG and the source of biogas is a municipal landfill site 101. To obtain such production rate, the mixed methane gas feed stream at the inlet of the LMG production plant 10 must be at a constant rate of about 700 $Nm^3/h$. Under normal operating conditions, the landfill site 101 of the example can delivered 2000 $Nm^3/h$ of biogas with a methane content of 50% vol., hence a normal supply of 1000 $Nm^3/h$ of methane which is more than enough for meeting the demand of the LMG production plant 10. The gas supply system 100 can also use methane gas coming from a natural gas pipeline 103 with a nominal pressure of 200 kPag at the utility delivery point. The natural gas pipeline 103 can supply the LMG production plant 10 alone if required.

First Example

In the first example, the LMG production plant 10 is operating at 100% capacity and the methane gas content in the biogas is sufficient to meet the process demand. In this situation, the demand controller 502 opens valve 117 to feed 700 $Nm^3/h$ of methane gas from the landfill site 101. The biogas subsystem 104 is adjusted so that the demand is met. Since the biogas demand is inferior to the biogas production, the methane content will rise over time and will stabilized at more than 50% vol. of methane, for example 54% vol. No natural gas is required in this example, hence valves 122 and 123 are closed completely.

Second Example

The second example assumes that the biogas supply is only partially available. For instance, such scenario can occur if there is a maintenance issue and some of the hydrostatic multi-phase separators 202 are shut down and the landfill site 101 can now only deliver 1000 $Nm^3/h$ of biogas having a methane content of 50% vol. Since the biogas requirement is more than what is available, the methane content of the delivered biogas will drop over time. At one point, the methane content in the biogas will fall under 50% vol.

To avoid depleting the gas field, the methane gas supply controller 502 will act on valves and the compressor within the biogas subsystem 104 to limit the methane supply and keep the methane content at its set point of 50% vol. Since the pressure downstream of the gas mixing vessel 106 will eventually start to fall due to a lack of methane, the system controller will automatically start to open the natural gas flow control valve 122 and compensate the methane gas shortages with natural gas. The biogas flow rate will continue to drop over time and will eventually reach its equilibrium of supplying 500 $Nm^3/h$ of methane gas. After this point is reached, the system will reach its equilibrium until more methane gas is available. Meanwhile, the natural gas feed stream will go from zero and to 200 $Nm^3/h$ of methane gas. Depending on its setting, it is possible that the valve 122 could be insufficient to meet the natural gas demand. In such case, the valve 123 could open to increase the flow rate and meet the demand. When the problems at the biogas source are fixed and the biogas source is back to normal, the nominal biogas capacity will eventually be back to normal as well. The methane gas content in the biogas will then rise above the 50% vol. set point and, since more methane gas is available, the valve 117 will open more to supply an increased proportion of the biogas into the mixed methane gas feed stream. Valves 122 and 123 will close as required over time.

As can be appreciated, a large disruption in the biogas stream will not interrupt the operation of the LMG production plant 10, even if the biogas is shut down completely. Also, since the natural gas is fed at a relatively low pressure, there is no condensation of the water vapor present in the biogas within the gas mixing vessel 106.

Third Example

In this third example, there is the same biogas system disruption as described in the second example but the natural gas is supplied using a high pressure natural gas network, for instance one where the natural gas supply pressure is 3450 kPag instead of 200 kPag. The natural gas pressure reduction can cool the natural gas stream from 5° C. at high pressure to −13.7° C. at 100 kPag. With a mixture of 500 $Nm^3/h$ of methane gas at 100 kPag and +40° C. from the biogas source and 200 $Nm^3/h$ of methane gas at 100 kPag and −13.7° C. from the natural gas source, the theoretical gas mixture temperature would be +24.3° C. at the outlet of the gas mixture vessel 106. This mixture would produce about 4 kg/h of condensate that would be discharged from the gas mixing vessel 106 through the condensate outlet 140. However, since the natural gas being feed into the gas mixing vessel 106 from the calibrated orifices 133 is at a relatively low temperature, it is likely that condensate will be created near these orifices and that they could freeze near at these locations.

In general, a decrease in the biogas flow will increase the risks of having condensate freezing at some point since the heat contained within the biogas feed stream will no longer be sufficient to heat the mixture above the condensate freezing point and frozen condensate could fill the gas mixing vessel 106 entirely. This situation can be mitigated by providing, for instance heating device 128 as shown in FIG. 3 or a heat exchanger 127 as shown in FIG. 4. By providing some form of heating for the reduced pressure natural gas stream, the gas mixing vessel 106 can be maintained fully operational regardless of the operating conditions.

The present detailed description and the appended figures are meant to be exemplary only. A skilled person will recognize that variants can be made in light of a review of the present disclosure without departing from the proposed concept.

REFERENCE NUMERALS

10 LMG production plant
100 gas supply system
101 landfill site
102 anaerobic digester
103 natural gas pipeline
104 biogas subsystem
105 control device
106 gas mixing vessel
108 landfill gas composition analyzer
109 landfill gas quality control valve
110 digester gas composition analyzer
111 digester gas quality control valve
112 low pressure compressor
113 biogas cooler
114 biogas flowmeter
115 biogas pressure sensor
116 biogas temperature sensor
117 biogas flow control valve
118 natural gas pressure reducing valve
119 natural gas flowmeter
120 natural gas pressure sensor
121 natural gas temperature sensor
122 natural gas flow control valve
123 natural gas flow control valve
124 natural gas flow control valve
127 heat exchanger
128 heating device
130 circular distribution pipe
131 circular distribution pipe
132 circular distribution pipe
133 calibrated orifices
134 vane
135 vane
136 vane
137 common header
138 internal central conduit
140 condensate outlet
142 mixed methane gas feed stream outlet
144 main vertically-extending portion
150 biogas pretreatment unit
152 additional biogas cooling unit
154 pressure sensor
156 pressure sensor
160 pressure sensor
200 gas treatment system
202 hydrostatic multi-phase separator
300 LMG production and nitrogen rejection system
301 first heat exchanger
302 sixth heat exchanger
303 second heat exchanger
304 fractional distillation column
305 fourth heat exchanger
306 expansion valve
307 fifth heat exchanger
308 nitrogen phase-separator vessel
309 third heat exchanger
310 LMG storage tank
316 venting outlet
400 independent cryogenic refrigeration system
500 LMG production integrated control system
501 LMG demand controller
502 methane gas supply controller
503 gas treatment system controller
504 LMG production and nitrogen rejection system controller
505 independent cryogenic refrigeration system controller
600 cylindrical portion
602 upper lid portion
604 bolts
606 funnel-shaped portion
608 bottom end portion
610 inner chamber
620 condensate level
622 bottom-opened inlet end
700 LMG mass flowrate measuring device

What is claimed is:

1. A gas supply system for generating a mixed methane gas feed stream using at least one source of biogas and at least one alternate source of methane gas, the gas supply system including:
   a biogas subsystem;
   a control device for the methane gas coming from the at least one alternate source of methane gas; and
   a vertically-extending gas mixing vessel having an upper biogas inlet that is selectively in fluid communication with an outlet of the biogas subsystem, at least two vertically spaced-apart mid-level gas inlets that are each selectively in fluid communication with the control device for the methane gas coming from the at least one alternate source of methane gas, a bottom condensate outlet, and a mixed methane gas feed stream outlet that is located vertically above the mid-level gas inlets.

2. The gas supply system as defined in claim 1, wherein the mixed methane gas feed stream outlet of the gas mixing vessel is located at an outlet of an internal central conduit, the internal central conduit including a main vertically-extending portion having an bottom-opened inlet end that is located vertically above a bottom end of the gas mixing vessel, the internal central conduit defining an exit path for the mixed methane gas feed stream extending between the bottom-opened inlet end and the mixed methane gas feed stream outlet.

3. The gas supply system as defined in claim 2, further including a plurality of vertically spaced-apart sets of vanes attached around the main vertically-extending portion of the internal central conduit, each set of vanes being in registry with a corresponding one of the mid-level gas inlets of the gas mixing vessel.

4. The gas supply system as defined in claim 3, wherein the sets of vanes are disposed in alternate directions to promote gas intermixing between a biogas stream path extending from the upper biogas inlet towards bottom-opened inlet end of the internal central conduit.

5. The gas supply system as defined in claim 1, wherein each mid-level gas inlet includes a circular distribution pipes having a corresponding set of axisymmetric orifices leading directly inside an inner chamber of the gas mixing vessel.

6. The gas supply system as defined in claim 5, wherein in each set of orifices, the orifices are located on an upper inner quadrant of the corresponding pipe.

7. The gas supply system as defined in claim 1, wherein the biogas subsystem includes a biogas composition analyzer and a biogas pressure sensor.

8. The gas supply system as defined in claim 1, wherein the biogas subsystem further includes a biogas pretreatment unit to remove a portion of at least one among carbon dioxide and hydrogen sulfide from the biogas stream.

9. The gas supply system as defined in claim 8, wherein the biogas subsystem further includes a biogas compressor and a biogas cooler that is located immediately downstream of the biogas compressor, the biogas pretreatment unit being located immediately downstream of the biogas cooler.

10. The gas supply system as defined in claim 9, wherein the biogas subsystem includes two sources of biogas, each source having a corresponding incoming biogas circuit merging at the biogas compressor.

11. The gas supply system as defined in claim 1, wherein the biogas subsystem further includes a hydrostatic multi-phase separator located at an inlet of the biogas subsystem to receive biogas from a landfill site.

12. The gas supply system as defined in claim 1, wherein the methane gas from the at least one alternate source of methane gas is natural gas, the control device including a natural gas pressure reducing valve, a natural gas flowmeter, a natural gas pressure sensor, a natural gas temperature sensor, and a plurality of natural gas flow control valves, each natural gas flow control valve being provided immediately upstream a corresponding one of the mid-level gas inlets of the gas mixing vessel.

13. The gas supply system as defined in claim 12, wherein the natural gas pressure reducing valve is configured and disposed to receive a natural gas stream from a natural gas pipeline, the natural gas pressure reducing valve being located at an inlet of the control device.

14. The gas supply system as defined in claim 13, wherein the natural gas pressure reducing valve has at least one among the following features (A) and (B):
  (A) the natural gas pressure reducing valve is located immediately upstream of a natural gas heating device;
  (B) the natural gas pressure reducing valve is located immediately upstream of a heat exchanger in which the natural gas stream is in indirect heat exchange relationship with the biogas stream inside the biogas subsystem.

* * * * *